United States Patent
Sigg

[11] Patent Number: 6,161,731
[45] Date of Patent: Dec. 19, 2000

[54] DOSING DEVICE

[75] Inventor: Jürgen Sigg, Lörrach, Germany

[73] Assignee: Novartis AG, Basel, Switzerland

[21] Appl. No.: 09/230,691

[22] PCT Filed: Jul. 23, 1997

[86] PCT No.: PCT/EP97/03984

§ 371 Date: Jan. 29, 1999

§ 102(e) Date: Jan. 29, 1999

[87] PCT Pub. No.: WO98/05433

PCT Pub. Date: Feb. 12, 1998

[30] Foreign Application Priority Data

Jul. 31, 1996 [EP] European Pat. Off. .............. 96810512

[51] Int. Cl.[7] ........................................................ B67D 5/38
[52] U.S. Cl. ........................ 222/158; 222/257; 222/260; 222/321.1; 222/321.3
[58] Field of Search .................................. 222/158, 320, 222/321.1, 321.3, 321.7, 32.8, 257, 260; 604/187, 68

[56] References Cited

U.S. PATENT DOCUMENTS

| | | | |
|---|---|---|---|
| 3,368,591 | 2/1968 | Zerbetto | 222/158 |
| 3,838,689 | 10/1974 | Cohen | 128/218 |
| 3,874,381 | 4/1975 | Baum | 128/206 |
| 5,016,782 | 5/1991 | Pfanstiel | 222/257 |
| 5,032,117 | 7/1991 | Motta | 604/88 |
| 5,127,548 | 7/1992 | Brunet et al. | 222/80 |
| 5,244,122 | 9/1993 | Botts | 222/158 |
| 5,465,873 | 11/1995 | Mejean et al. | 222/47 |
| 5,531,708 | 7/1996 | Woodruff | 604/208 |
| 5,601,077 | 2/1997 | Imbert | 604/68 |

FOREIGN PATENT DOCUMENTS

| | | |
|---|---|---|
| 0 562 943 A1 | 9/1993 | European Pat. Off. . |
| 0 567 369 A1 | 10/1993 | European Pat. Off. . |
| 9-299484 | 11/1997 | Japan . |

*Primary Examiner*—Kevin Shaver
*Assistant Examiner*—David Deal
*Attorney, Agent, or Firm*—Michael U. Lee

[57] ABSTRACT

A dosing device (1, 31) comprises a storage vessel (16, 36) for a substance to be dosed and a feed means (5) which transports the substance to a discharge opening (3) of the dosing device. A storage vessel (16, 36) is connected to the feed means (5) in such a way that the vessel is sealed off from the outside on all sides and there is provided in the wall of the storage vessel (16, 36) a closure element (21, 41) which, when the storage vessel (16, 36) is emptied, is subjected to a force which is caused by the external air pressure and has the effect that the shape of the storage vessel (16, 36) can be changed in the region of the closure element (21, 41). Further there is provided indicating means (18, 38) assigned to the movement of the closure element (21, 41) with the effect that the extent of movement of the closure element (21, 41), and consequently the amount of substance discharged, can be indicated.

2 Claims, 3 Drawing Sheets

DOSING DEVICE

BACKGROUND OF THE INVENTION

This invention relates to a dosing device for flowable substances, in particular liquids to be sprayed, having a storage vessel for the substance to be dosed and feed means which transports the substance to the discharge opening of the dosing device.

Such dosing devices are known in the form of pump-spray systems which allow liquids, pharmaceutical solutions for example, to be sprayed The known systems first have to be primed by filling the dosing pump, the user being unable to check from which point in time the dosing pump is completely filled and therefore from which point in time the full amount of solution assigned to a pumping movement is sprayed. Therefore, with known pump-spray systems it is not possible to achieve the dosing accuracy of five per cent typically required by registration authorities for medicaments with the dosing pumps available on the market.

Furthermore, the previously known pump-spray systems do not allow a dry substance to be dissolved or suspended in a suitable solvent just before application to the patient and, after the substance has been dissolved or suspended, to be applied precisely and under sterile conditions from a gas-free, e.g. airless, reservoir.

SUMMARY OF THE INVENTION

The present Applicants have sought to overcome shortcomings of known devices for administration to, e.g. wounds.

The present invention is based on the object of providing a dosing device which can be easily used in a straightforward manner and allows a quantitatively exact and aseptic application of an active agent in solution or suspension, i.e. which contains drug product, even at body surfaces where access is difficult.

This object is achieved according to this invention by connecting a storage vessel to feed means in such a way that the vessel is sealed off from the outside on all sides and there being provided in the wall of the storage vessel a closure element which, when the storage vessel is emptied, is subjected to a force caused by the external air pressure and has the effect that the shape of the storage vessel can be changed in the region of the closure element, and by there being provided indicating means which is assigned to the movement of the closure element and has the effect that the extent of the movement of the closure element, and consequently the amount of substance discharged, can be indicated.

It is particularly advantageous to use as the feed means a dosing pump for a gas-free sealed system which can be actuated by an abrupt pushing movement of a chosen spray head. In one embodiment of this invention, the storage vessel is formed by the syringe body of a plunger syringe and the closure element is formed by the syringe plunger of the plunger syringe.

The indicating device assigned to the syringe plunger serving as the closure element makes it possible to achieve dosing accuracy of five per cent required by registration authorities for medicaments irrespective of the dosing accuracy of the dosing pump, since the dosage is no longer measured by counting the thrusts of the dosing pump but by reading off from the scale assigned to the closure element, in particular the syringe plunger.

In another embodiment of the invention, the plunger rod of the plunger syringe is detachably connected to the syringe plunger in order to prevent the plunger rod from causing any hindrance.

If the storage vessel is not manufactured all in one from a transparent material, it is advantageous if the respective position of the plunger can be seen from outside through a transparent region in the cylindrical portion of the storage vessel and the transparent region is provided with the scale. In the simplest case, the storage vessel comprises a transparent ready-to-use syringe provided with a printed-on scale.

The active agent may be in the form of a lyophilisate which may have to be reconstituted prior to administration e.g. to a wound.

It is also possible, however, to design the storage vessel as the first chamber of a double-chamber syringe which contains active agent to be reconstituted, and for the reconstitution liquid to be injected from the second chamber of the double-chamber syringe into the first chamber before use.

In the case of a dosing device having a single-chamber syringe, it is advantageous to connect the plunger syringe detachably to the dosing pump by providing an appropriate connection, e.g. a Luer-lock cone on the front end of the ready-to-use syringe. This makes it possible to prepare the pharmaceutical solution freshly just before application, for example by using a suitable solvent to dissolve a dry substance.

The present Applicants contemplate administration of any active agent in a liquid composition, in particular an active agent useful in treatment of skin conditions, e.g. a cytokine or transforming growth factor (TGF) composition, for example a TGF-beta 3 composition using the device of the invention. Other substances which may be administered include, for example, calcitonins e.g. salmon calcitonin or human calcitonin.

In another aspect, therefore, this invention provides a method of topical administration of a cytokine or TGF-beta composition, e.g. TGF-beta 3, using the device herein described.

In another aspect this invention provides a method for topical, nasal or buccal administration of lyophilised active agent in multiple doses, e.g. human calcitonin, salmon calcitonin or human growth hormone.

Although the invention is described below with reference to a embodiment of a dosing device for liquids to be sprayed, it may also be used for other flowable substances, in particular pastes, gels and creams.

BRIEF DESCRIPTION OF THE FIGURES

Following is a description by way of example only with reference to the drawings in which.

DETAILED DESCRIPTION OF THE INVENTION

Figure 1:
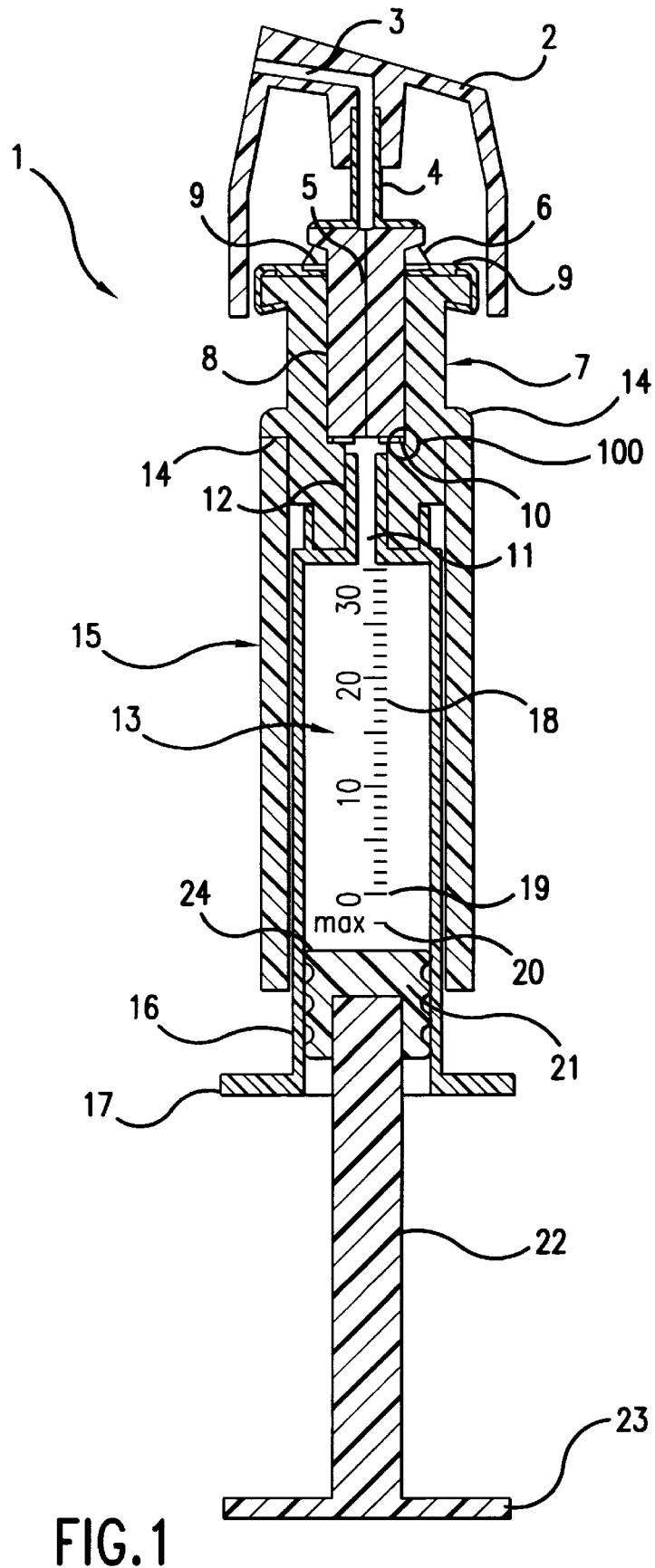
FIG. 1 shows in a longitudinal section a dosing device according to the invention before application of the active agent begins.

A dosing device 1 for flowable substances is shown in FIG. 1 and is intended for carrying out a topical and sterile application of TOF-beta 3 (Transforming Growth Factor beta 3) appropriate for the area of a wound. With the aid of the dosing device 1 represented in FIG. 1, the active ingredient is to be brought into a dosage form suitable for the local topical treatment of chronic wounds, for example ulcus cruris, decubitus-ulcers and diabetic foot ulcers, burns or surgical wounds, in order to provide a user-friendly system.

The dosing device 1 has a spray head 2, which discharges a spray free from carrier gas, i.e. is an airless spray, by mechanically breaking down a stream of liquid. For the abovementioned application, a so-called "moist spray" with particle sizes of over 50 μm is ideal. The spray head 2 has a spray channel 3, which is compatible with to the viscosity of the formulation used for the substance to be atomized.

The spray channel 3 is connected to a small pump tube 4 of a dosing pump 5. The dosing pump 5 is a dosing pump for a gas-free, i.e. airless, sealed system.

By intermittently actuating the spray head 2 in the axial direction of the small pump tube 4, the dosing pump 5 is actuated and, as a result, the pumped liquid is atomized via the small pump tube 4 and the spray channel 3.

The dosing pump 5 is connected to a connection element 7, for example with the aid of a metal cap 6. The connection element 7 has a cylindrical bore 8, in which the cylindrical dosing pump 5 is connected with a good sealing action with the aid of the flanged-on metal cap 6. A sealing ring 9 may be provided between the metal cap 6 and the end face of the connection element 7. A further seal 10, for example made of rubber or elastomeric material, is provided for sealing off the dosing pump 5 at a shoulder 100, against which the dosing pump 5 is supported and at which the cylindrical bore 8 changes from a larger diameter, adapted to the dosing pump 5, of a bore portion 11 to smaller diameter.

The bore portion 11 of the substantially cylindrically shaped connection element 7 serves for receiving a cannula connection 12 of a pump syringe 13 in a sealed-off manner.

The connection between the plunger syringe 13 and connection element 7 is preferably realized by a coupling with the aid of a connection for medical devices, e.g. a Luer-lock cone, schematically represented in drawing FIG. 1. In this way, a secure and sealed, but nevertheless easily releasable connection is achieved between the plunger syringe 13 and the connection element 7.

The connection element 7 has a peripheral stop ring 14, against which there strikes a transparent tube element 15, which is fixedly connected to the connection element 7 and serves to receive and centre plunger syringe 13 in order to permit easier handling of the dosing device 1. In the axial direction, the tube element 15 extends over a length which reaches right up to near the flange parts 17 formed on to syringe body 16.

Syringe body 16 of plunger syringe 13 is preferably likewise produced from a transparent material. The plunger syringe 13 may be a prefilled ready-to-use syringe and, at the point in time represented in FIG. 1, contains the respectively required specific pharmaceutical active agent solution.

In another embodiment not represented in the drawings, plunger syringe 13 contains a gel or a cream instead of a liquid, spray head 2 and the spray channel in this case being modified in such a way that atomization does not take place, but instead a precise discharge.

As can be seen in FIG. 1, a scale 18 which is printed on the syringe body 16, can be seen through the transparent tube element 15. The scale 18 serves to indicate the volume removed from the space inside the syringe body 16 when the dosing pump 5 is actuated, and consequently the dose of the specific active agent solution. Scale 18 may in this case relate to area units to be treated on the skin of the patient.

In FIG. 1 there can be seen below zero mark 19 of scale 18 a marking 20 which is labelled "max." (maximum) and which corresponds to the optimum maximum filled state of the plunger syringe 13 when the plunger syringe 13 is connected to the connection piece 7 and the dosing pump 5. For better legibility, the syringe plunger 21 of the plunger syringe 13 is shown in FIG. 1 in a position slightly further back than the optimum position when the cannula connection 12 is connected to the bore portion 11.

Syringe plunger 21 is detachably connected to a plunger rod 22, for example an unscrewable plunger rod 22. The plunger rod 22 has a gripping part 23, with the aid of which the syringe plunger 21 can be actuated manually.

After inserting the plunger syringe 13, filled up to the marking 20, into tube element 15 and connecting the cannula connection 12 to the inlet side of the dosing pump 5 in a sealed manner, the plunger rod 22 is unscrewed from the syringe plunger 21 in a preferred embodiment of the invention, so that it is no longer possible for the syringe plunger 21 to be acted on inadvertently from outside.

Before the dosing device 1 represented in FIG. 1 is used on the patient, the dosing device 1 is primed by repeatedly actuating the spray head 2 in the axial direction, thereby activating the dosing pump 5. After just a few thrusts by the pump, it is completely filled with liquid in just the same way as the space inside the syringe body 16 and is entirely freed of residual gas, in particular residual air. In this way, the occurrence of incorrect dosages during a spraying operation when the dosing device 1 is used for the first time or else after remaining unused for some time, e.g. hours, days or longer, can be avoided.

For this purpose, when using the dosing device 1 for the first time, all that is necessary to obtain a specific syringe content is to end the actuating of the dosing pump 5 before the application operation when the ram face 24 of the syringe plunger 21 pointing upwards in FIG. 1 is in line with the zero mark 19. As soon as this is the case, the dosing device 1 can be used to carry out a quantitatively exact sterile application of the active agent solution.

In this case, it is of no consequence whether individual pumping thrusts produce different discharge amounts, since the amount of active agent solution discharged via the spray head 2 can be measured directly through the reduction in volume of the content of the syringe body 16. This is so because, on account of the external air pressure, the production in the amount of liquid in the syringe body 16 brought about by the discharge of the active agent solution causes an axial displacement of syringe body 21 in the direction of its cannular connection 12.

Figure 2:
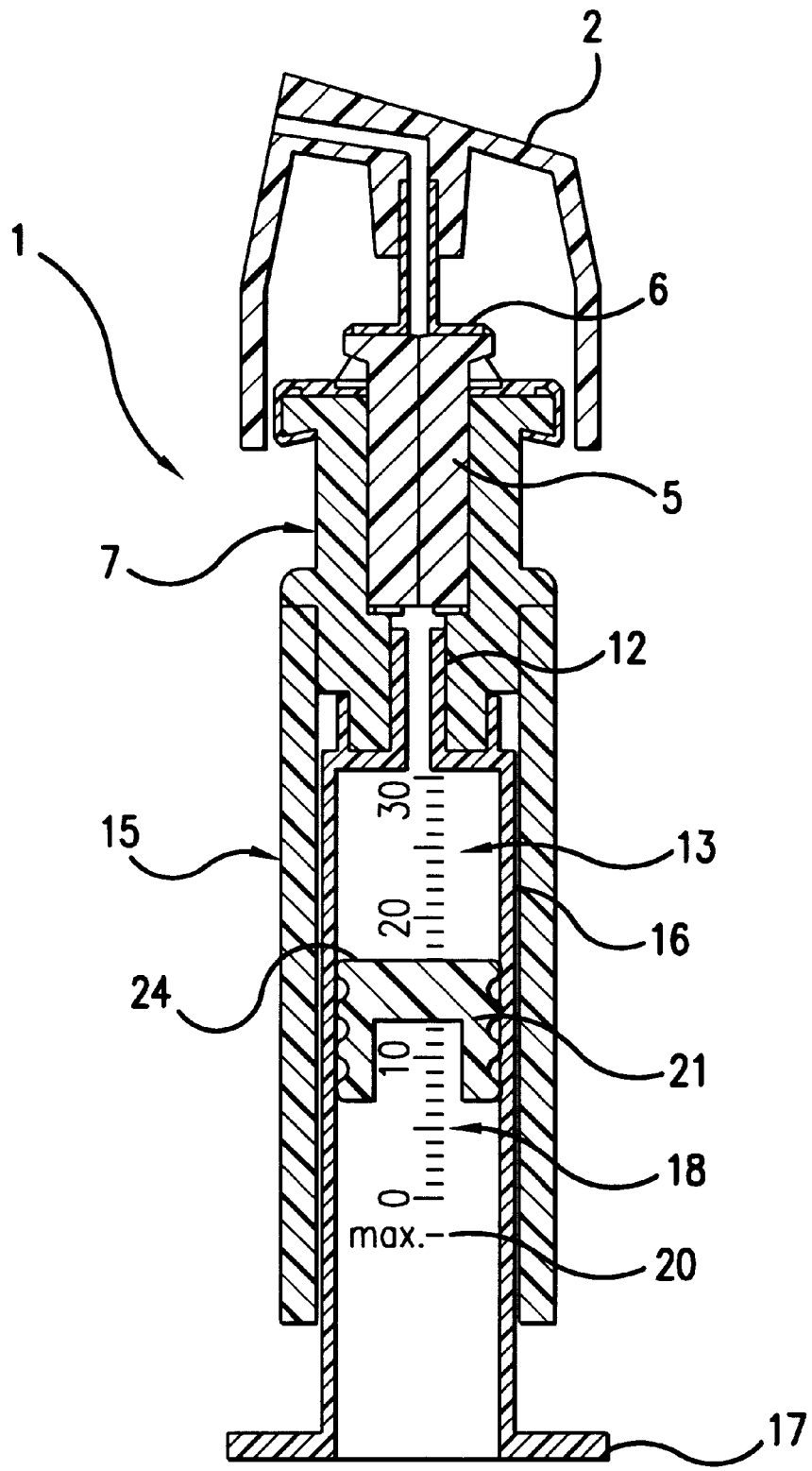
FIG. 2 shows the dosing device according to FIG. 1 after application of the active agent.

The representation in FIG. 2 shows the dosing device 1 after pumping movements. The syringe plunger 21, which is arranged in such a way that it slides well and is sealed, is located with its ram face 24 at a point of the scale 18 by which is indicated exactly the amount of active agent solution applied. If this amount does not correspond yet to the desired value, it is possible to produce exactly the amount of spray considered necessary by further pump thrusts, in particular also pump thrusts of which the stroke does not correspond to a full stroke.

FIG. 2 shows the syringe plunger 21 at the end of a treatment in which, for example, an area of 17 area units were to be treated or in which an amount of 17 volume units were to be sprayed.

The pharmaceutically active agent composition, a solution or suspension, may be prepared in the form of a sterile, prefilled ready-to-use syringe, which is inserted into the dosing device 1 before use. If the solution of a freeze-dried preparation is to be sprayed, the filling of the plunger syringe 13 may be carried out before it is inserted into the dosing device 1 by using as the plunger syringe 13 a prefilled ready-to-use syringe on the cannula connection 12 of which a cannula is first fitted. With the aid of the cannula, the closure of an injection vial with a lyophilisate is pierced. The lyophilisate contains the active ingredients intended for the application in a stable and biologically active form. After the content of the syringe has been injected into the injection vial, the lyophilisate is reconstituted by gentle shaking or swirling. Subsequently, the content of the injection vial is drawn up again into the plunger syringe 13. If too much solution is drawn up, the excess is forced out until the ram face 24 of the syringe plunger 21 is beneath the marking "max" 20 provided on the syringe body 16.

Thereafter, the cannula is removed and the plunger syringe 13 is introduced into the tube element 15 of the dosing device 1 and the cannula connection 12 is connected to the connection piece 7 in a sealed manner. For better handling, the plunger rod 22 is unscrewed from the syringe plunger 21 in the way which can be seen from FIG. 2. The dosing pump 5 can be filled in the way explained above by repeatedly depressing the spray head 2 and, as a result, the syringe plunger 21 can be moved slowly in the direction of the cannula connection 12. The depressing is repeated until the edge of the ram face 24 comes to lie on the zero mark 19 of the scale 18.

The dosing device 1 is then ready to use, and the treatment of the patient can begin, the size of the area to be treated being determined first of all. The areas to be treated on the patient are sprayed and the dose taken is read off from the scale 18. After treatment, the dosing device 1 used can be disposed of.

Figure 3:
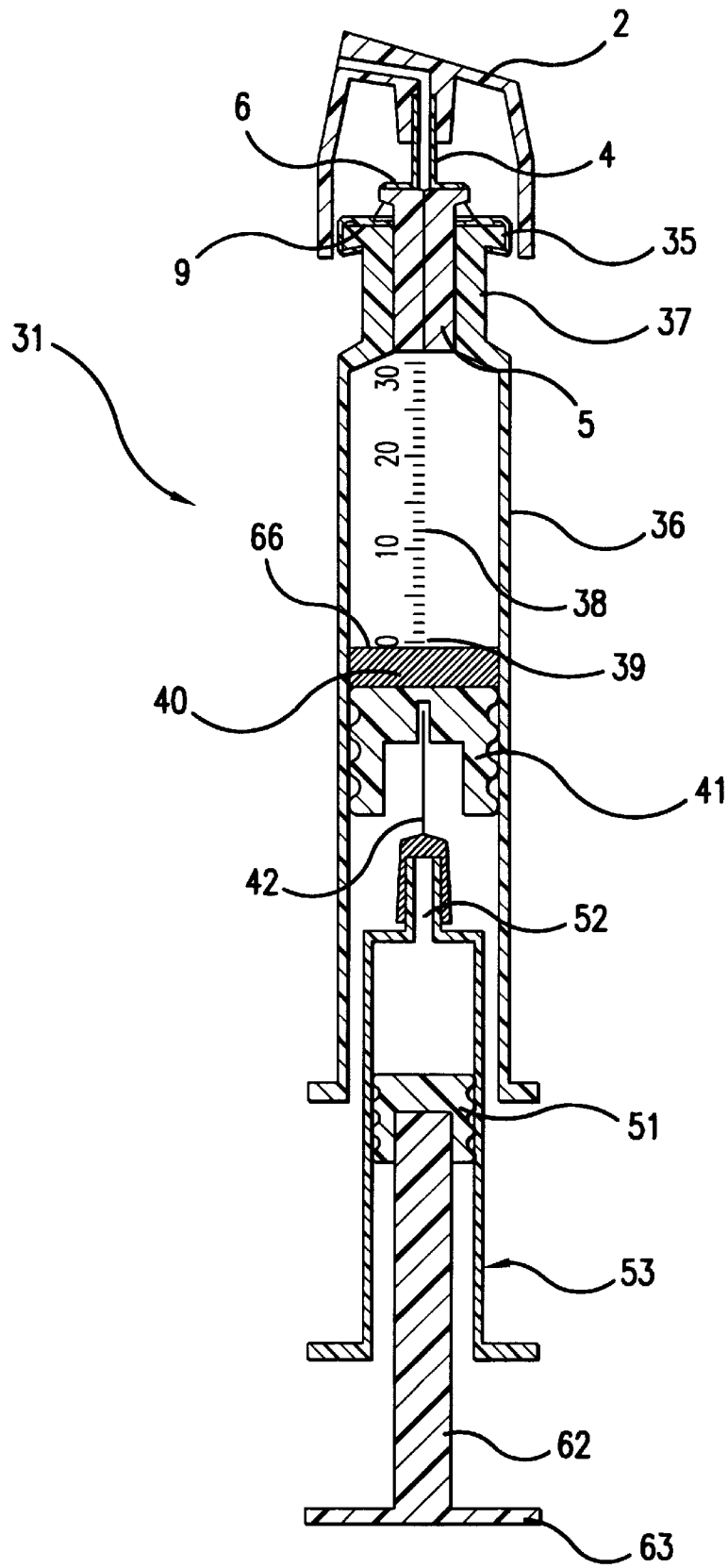
FIG. 3 shows in longitudinal section a device according to the invention with a structural design corresponding to a double-chamber syringe.

In the embodiment represented in FIG. 3, dosing device 31 is designed in the form of a double-chamber syringe. The dosing pump 5 is connected to a spray head 2 via a small pump tube 4, in the way known from FIGS. 1 and 2.

The dosing pump 5 is fastened with the aid of the metal cap 6 on a connection element 37, which is formed on the front end of a syringe body 36. The metal cap 6 is bordered by a flange part 35 on the front end of the connection element 37. A sealing ring 9 provides a good seal. On syringe body 36 there is provided a scale 38 which has the same function as the scale 18 in the embodiment represented in FIGS. 1 and 2. In a corresponding way, a zero mark 39 and a marking 40 for the maximum filling are provided.

Arranged in the syringe body 36 is a syringe plunger 41 which can be pierced with the aid of a cannula 42. The cannula 42 is connected to the cannula connection 52 of a plunger syringe 53. The dimensions of the parts mentioned above are chosen such that the length of the connection element 37 is much greater than the length of the scale 38 and therefore the plunger syringe 53 protrudes over about half the length of the connection element 37 and over about half its own length into the connection element 37 when the syringe plunger 41 is close to the marking 40.

The plunger syringe 53 has a syringe plunger 51 and a plunger rod 62 with gripping part 63 connected to the said plunger.

With the aid of the plunger syringe 53 designed as a prefilled ready-to-use syringe, a reconstitution liquid is injected via the cannula 42 through the syringe plunger 41 into the receiving space of the syringe body 36 at the beginning of use of the dosing device 31. In FIG. 3 there can be seen a lyophilisate 66, which is dissolved by gentle shaking or swirling. During the injection of the reconstitution liquid, the syringe plunger 41 moves downwards, starting from an upper position in FIG. 3, until it is in the position in which the syringe plunger 41 is close to the marking 40. When the filling operation has ended, the plunger syringe 53 can be removed and the dosing device 31 used in a way corresponding to the dosing device 1 for the application of an active ingredient to the skin of a patient.

Compositions for administration using the spray of this invention may be stored conveniently in a vial, and a known venting valve, e.g. as described in German utility model no. 8505794, may be employed to puncture the vial in oder to transfer the composition into the storage vessel.

What is claimed is:

1. A dosage device for topical application of a composition comprising a pharmaceutically active agent in solution or suspension to a body surface, which device comprises a spray head adapted to discharge an amount of the composition free of air, a pump for an air-free sealed system which pump is actuated by a pushing movement of the spray head, a connection element which surrounds the pump and comprises a bore portion and a Luer-lock cone, a transparent tube element connected to element and adapted to receive a syringe prefilled with the composition, wherein the syringe comprises a cannula, a syringe body having a scale printed thereon, and a plunger comprising a ram face which plunger is detachably connected to a rod, the arrangement being such that in use the prefilled syringe is attached to the connection element by connection of the cannula with the Luer-lock cone, the rod is detached from the plunger and after initial priming of the pump, the composition is sprayed onto the body surface and the dose applied is determined from viewing the scale adjacent to the ram face so as to measure from the plunger position reduction in volume of the syringe content and thus volume remaining, thereby providing accurate dosing at any orientation with respect to the body surface.

2. A dosage device as claimed in claim 1 administration of a cytokine, calcitonin or TGF-beta composition.

* * * * *